US007816077B2

(12) United States Patent
Kanaoka

(10) Patent No.: US 7,816,077 B2
(45) Date of Patent: Oct. 19, 2010

(54) METHOD OF DETECTING COLON CANCER MARKER

(75) Inventor: Shigeru Kanaoka, Shizuoka (JP)

(73) Assignees: Hamamatsu Foundation for Science and Technology Promotion, Hamamatsu (JP); Olympus Corporation, Tokyo (JP)

( * ) Notice: Subject to any disclaimer, the term of this patent is extended or adjusted under 35 U.S.C. 154(b) by 0 days.

(21) Appl. No.: 10/549,389

(22) PCT Filed: Sep. 19, 2003

(86) PCT No.: PCT/JP03/11972

§ 371 (c)(1),
(2), (4) Date: Sep. 14, 2005

(87) PCT Pub. No.: WO2004/083856

PCT Pub. Date: Sep. 30, 2004

(65) Prior Publication Data

US 2006/0216714 A1    Sep. 28, 2006

(30) Foreign Application Priority Data

Mar. 19, 2003 (JP) .............................. 2003-075552

(51) Int. Cl.
*C12Q 1/68* (2006.01)
(52) U.S. Cl. ......................................................... 435/6
(58) Field of Classification Search ........................ None
See application file for complete search history.

(56) References Cited

U.S. PATENT DOCUMENTS

| 4,843,155 | A | 6/1989 | Chomczynski | |
|---|---|---|---|---|
| 5,654,179 | A | 8/1997 | Lin | |
| 5,777,099 | A | 7/1998 | Mehra | |
| 6,258,541 | B1 * | 7/2001 | Chapkin et al. ............... | 435/6 |
| 6,329,179 | B1 | 12/2001 | Kopreski | |
| 6,406,857 | B1 | 6/2002 | Shuber et al. | |
| 7,101,663 | B2 * | 9/2006 | Godfrey et al. ............... | 435/6 |

FOREIGN PATENT DOCUMENTS

| EP | 0 389 063 A2 | 9/1990 |
|---|---|---|
| EP | 1 674 869 A1 | 6/2006 |
| JP | 2002-142767 A | 5/2002 |
| WO | WO 00/63358 A1 | 10/2000 |
| WO | WO 2005/019827 A1 | 3/2005 |
| WO | WO 2007/018257 A1 | 2/2007 |

OTHER PUBLICATIONS

Alexander and Raicht (1998) Digestive Diseases and Sciences vol. 43 No. 12 pp. 2652-2658.*
Biotecx Bulletin No. 28, 1993.*
Sano et al. (1995) Cancer Research 55: 3785-3789.*
Lagerholm et al. (Apr. 2001) Gastroenterology vol. 120 No. 5 supplement 1 Abstract No. 16 in p. A4.*
Ambion Poly A+ RNA Kit 2000.*
Murphy et al. entitled "Gene expression studies using microarrays: principles, problems, and prospects," (Adv Physiol Educ. Dec. 2002;26(1-4):256-70).*
Lucentini, who entitled an article, "Gene Association Studies Typically Wrong" (The Scientist, 18(24):20).*
Grigoryev et al. (Genome Biol. 2004;5(5):R34. Epub Apr. 27, 2004).*
D. Sidransky et al., "Identification of *ras* Oncogene Mutations in the Stool of Patients with Curable Colorectal Tumors," *Science*, 256, Apr. 3, 1992, 102-105.
S.M. Dong et al., "Detecting Colorectal Cancer in Stool With the Use of Multiple Genetic Targets," *Journal of the National Cancer Institute*, 93 (11), Jun. 6, 2001, 858-865.
G. Traverso et al., "Detection of *APC* Mutations in Fecal DNA From Patients With Colorectal Tumors," *The New England Journal of Medicine*, 346 (5), Jan. 31, 2002, 311-320.
G. Traverso et al., "Detection of Proximal Colorectal Cancers Through Analysis of Faecal DNA," *The Lancet*, 359, Feb. 2, 2002, 403-404.
Fang Sheng, Wu Pei, Liu Yongzhong, et al., "Clinical Investigation of Expression of Gastrin mRNA in Colorectal Carcinoma," *Proceedings of Wannan Medical College*, vol. 21, (2002), 20-23.
Hiroki Nakagawa, "Bio Jikken Illustrated 2 Idenshi Kaiseki no. Kiso", Shujunsha Co., Ltd., Sep. 25, 1995, pp. 153 to 166.
L.A. Davidson et al., "Non-invasive detection of fecal protein kinase C $\beta_{II}$ and ç messenger RNA: putative biomarkers for colon cancer," Carcinogenesis, vol. 19, No. 2, (1998), pp. 253 to 257.
T. Yamao et al., "Abnormal Expression of CD44 Variants in the Exfoliated Cells in the Feces of Patients With Colorectal Cancer," Gastroenterology, vol. 114, No. 6, (1998), pp. 1196 to 1205.
R.L. Alexander et al., "Purification of Total RNA from Human Stool Samples," Digestive Diseases and Sciences, vol. 43, No. 12, (1998), pp. 2652 to 2658.
Hajime Sano et al., "Expression of Cyclooxygenase-1 and -2 in Human Colorectal Cancer," Cancer Research, vol. 55, No. 17, (1995), pp. 3785 to 3789.
S. Kanaoka et al., "Shou P-379 Potential of colorectal cancer screening by using RT-PCR method in which COX-2 from feces is used as a marker," Japanese Journal of Gastroenterology, vol. 99, special extra issue, Sep. 20, 2002, p. A634 Sho P-379.

(Continued)

Primary Examiner—Christopher M. Babic
(74) Attorney, Agent, or Firm—Westerman, Hattori, Daniels & Adrian, LLP

(57) ABSTRACT

It is intended to provide a non-invasive and convenient method of detecting a tumor marker for diagnosing colon cancer which is superior in sensitivity and specificity to the existing fecal occult blood test. More specifically speaking, a method of detecting a tumor marker for diagnosing colon cancer which comprises collecting biological sample which is immediately frozen using liquid nitrogen in some cases, homogenizing the sample in the presence of an inhibitor of an RNA digesting enzyme to give a suspension, extracting RNA from the obtained suspension, subjecting the extracted RNA to reverse transcription to give cDNA, amplifying the obtained cDNA and then detecting the thus amplified cDNA. This method is characterized by involving no procedure of separating cell components from the biological sample.

5 Claims, 1 Drawing Sheet

OTHER PUBLICATIONS

Rainer Deuter et al., "A method for preparation of fecal DNA suitable for PCR," *Nucleic Acids Research*, 1995, vol. 23, No. 18, pp. 3800 to 3801.

Kanaoka S. et al., "Potential Usefulness of Detecting cyclooxygenase 2 Messenger RNA in Feces for Colorectal Cancer Screening," *Gastroenterology*, (2004), vol. 147, No. 2, pp. 422-427.

Nosho K. et al., "Association of Ets-related transcriptional factor E1AF expression with overexpression of matrix metalloproteinases, COX-2 and iNOS in the early stage of colorectal carcinogenesis," *Carcinogenesis*, (2005), vol. 26, No. 5, pp. 892-899.

Boedefeld W.M. et al., "Increased expression of E1A-F, MMP-7, and COX-2 in human colorectal cancer," *Proceedings of the American Association for Cancer Research Annual Meeting*, (2002), vol. 43, p. 730, #3623.

Li X. et al., "Co-Expression of Matrix Metalloproteinase-7 and Cyclooxygenase-2 in Human Colorectal Carcinoma" *Proceedings of the American Association for Cancer Research Annual Meeting*, (2002), vol. 42 , p. 614, #3302.

De Craene B. et al., "The Transcription Factor Snail Induces Tumor Cell Invasion through Modulation of the Epithelial Cell Differentiation Program," *Cancer Research*, (2005), vol. 65, No. 14, pp. 6237-6244.

Roy H.K. et al., "The Transcriptional Repressor SNAIL Is Overexpressed in Human Colon Cancer," *Digestive Diseases and Sciences*, (2005), vol. 50, No. 1, pp. 42-46.

Dutta S.K. et al., "Noninvasive Detection of Colorectal Cancer by Molecular tools: Coming of Age," *Gastroenterology*, (1998), vol. 114, No. 6, pp. 1333-1335.

Kanemoto S. et al., "Funbenchu no COX-2 mRNA o Hyoteki ni shita DaichoganShindan Kenshin no Kanosei ni Tsuite," *Nippon Shokaki Shudan Kenshin Gakkai Zasshi*, (2004), vol. 42, No. 2, p. 58 (S3-3).

Shattuck-Brandt, R.L. et al., "Differential Expression of Matrilysin and Cyclooxygenase-2- in Intestinal and Colorectal Neoplasms," *Molecular Carcinogenesis*, 1999, vol. 24, No. 3, 1999, pp. 177-187.

Kanaoka Shigeru et al., "RNA-based stool assay is superior to a single immunochemical fecal occult blood test for detecting early colorectal cancer and adenoma," *Gastroenterology*, vol. 130, No. 4, Suppl. 2, Apr. 2006, p. A471, Digestive Disease Week Meeting/107th Annual Meeting of the American-Gastroenterological-Association; Los Angeles, CA, USA, May 19-24, 2006.

Takai Tetsunari et al., "Potential usefulness of detecting cyclooxygenase 2 and matrix metalloproteinase 7 messenger RNA in feces for colorectal cancer screening," *Gastroenterology*, vol. 130, No. 4, Suppl. 2, Apr. 2006, p. A188, Digestive Disease Week Meeting/107th Annual Meeting of the American-Gastroenterological-Association, Los Angeles, CA, USA, May 19-24, 2006.

Kanaoka Shigeru et al., "A comparison of fecal RNA test with immunochemical fecal occult blood test for detecting colorectal cancer and adenoma," *Gastroenterology*, vol. 132, No. 4, Suppl. 2, Apr. 2007, p. A623, Digestive Week Meeting/108th Annual Meeting of the American-Gastroenterological-Association, Washington, DC., USA, May 19-24, 2007.

Kanaoka Shigeru et al., Potential usefulness of predicting stage of colorectal cancer by fecal RNA test, *Gastroenterology*, vol. 134, No. 4, Suppl. 1, Apr. 2008, p. A183, Digestive Disease Week Meeting/109th Annual Meeting of the American-Gastroenterological-Association, San Diego, CA, USA, May 17-22, 2008.

European Examination Report dated Mar. 5, 2010, issued for corresponding European Patent Application 06 782 598.4.

Ioannidis, John P.A. et al.; "Replication validity of genetic association studies"; Nature Genetics, vol. 29, Nov. 2001, p. 306-309.

Leung, Wai K. et al.; "Detection of Hypermethylated DNA or Cyclooxygenase-2 Messenger RNA in Fecal Samples of Patients With Colorectal Cancer of Polyps"; The American Journal of Gastroenterology, vol. 102, May 2007, p. 1070-1076 (Abstract Only).

Wacholder, Sholom et al.; "Assessing the Probability That a Positive Report is False: An Approach for Molecular Epidemiology Studies"; Journal of National Cancer Institute, vol. 96, No. 6, Mar. 17, 2004, p. 434-442.

USPTO Office Action, issued May 28, 2010 for co-pending U.S. Appl. No. 12/460,143.

* cited by examiner

METHOD OF DETECTING COLON CANCER MARKER

This application is the United States national phase application of International Application PCT/JP03/11972 filed on Sep. 19, 2003.

FIELD OF THE INVENTION

The present invention relates to a tumor marker detecting method for diagnosing colon cancer comprising a process of extracting RNA from a biological sample, characterized by involving no procedure of separating cell components from the biological sample.

BACKGROUND OF THE INVENTION

The deaths by colon cancer are increasing. The number of deaths by colon cancer is the fourth large among male, and the second large among female deaths in all cancer deaths (Statistics of Japanese cancer deaths in 1999). According to an estimation of cancer patients in 2015 in Japan, number of colon cancer patients is estimated to be the first in both male and female. Global measures to counter colon cancer including secondary prevention are thus required, and mass screening of cancer may be one of the most effective methods.

For the mass screening of cancer, it is important that the detection method is easy and non-invasive. The only non-invasive method now available is the method to examine existence of occult blood in feces, that is, the fecal occult blood test, and is used extensively as a standard method of the mass screening of colon cancer.

However, the fecal occult blood test has rather low sensitivity and specificity (the sensitivity: 30 to 90%, the specificity: 70 to 98%), because appearance of hemoglobin in feces is not specific to tumor. Therefore, there is a shortcoming that quite a few false negatives and false positives exist.

Also, in the diagnosis of colon cancer, after or in parallel with the screening by the immunological fecal occult blood test, total colonoscopy or a combination of Ba-enema and sigmoidoscopy has been adopted. There is thus a shortcoming that it needs much time and effort.

As alternative methods to the fecal occult blood test, methods using DNA are reported, such as detection of mutations in K-ras, p-53, or APC genes, or detection of microsatellite instability in feces (D. Sidransky, et al., Science, 256, Apr. 3, 1992, 102-105; S. M. Dong, et al., Journal of the National Cancer Institute, 93 (11), Jun. 11, 2001, 858-865; G. Traverso, et al., The New England Journal of Medicine, 346 (5), Jan. 31, 2002, 311-320; G. Traverso, et al., The Lancet, 359, Feb. 2, 2002, 403-404).

These methods using DNA are non-invasive and can capture the direct changes in cancer cells, and have characteristics of having high specificity, and so are considered to be a hopeful method in the future. However, it has a demerit that the sensitivity is lower compared to the fecal occult blood test, a prior art, and is rather time and effort-consuming.

Further, as an alternative method to the fecal occult blood test, in order to detect gene expression more directly, a method for detecting mRNA of protein kinase C (PKC) or the like in the feces has been developed (L. A. Davidson, et al., Carcinogenesis, 19(2), 1998, 253-257; R. J. Alexander and R. F. Raicht, Digestive Diseases and Sciences, 43(12), 1998, 2652-2658; T. Yamao, et al., Gastroenterology, 114(6), 1998, 1196-1205).

However, the method making use of RNA described above could not have the sensitivity exceeding that of the fecal occult blood test method, because it was impossible to extract RNA easily and efficiently from a small amount of feces.

A method to detect RNA qualitatively and quantitatively by combining the PCR method with the reverse transcriptase reaction (RT), has been known. This RT-PCR method is superior to Northern blot technique in the high sensitivity to be able to detect trace molecules, and is more advantageous than the in situ hybridization technique in speed and easiness of manipulation.

However, since RNA is more unstable compared with DNA and is always subjected to a danger of decomposition by RNA digesting enzymes (RNases) which are ubiquitous in all the biological samples and very stable, strict control to avoid contamination of RNases is necessary in the RT-PCR method, during and after purification processes of RNA.

Therefore, when RNA is extracted from the feces, which is a biologically very crude sample, a process to separate the cell fraction in advance has been necessary, to exclude effects of RNases.

Accordingly, it has been considered impossible to extract RNA directly from feces containing enormous amount of RNases derived from very large amount of microorganisms, and, a separation of the cell fraction has been considered to be essential for removing at least exogenous RNases derived from microorganisms or the like.

Surprisingly, however, the inventor of the present invention found that in some cases, homogenization of frozen biological materials in the presence of RNase inhibitors can resolve the problems described above, and has completed the present invention.

SUMMARY OF THE INVENTION

It is therefore an object of the present invention to provide a non-invasive and convenient tumor marker detecting method for diagnosing colon cancer, which is superior in sensitivity and specificity to the existing fecal occult blood test.

The present invention is a method to prepare a sample for extracting RNA used to detect a tumor marker for diagnosing colon cancer, comprising following process;

a) a process to homogenize the collected biological sample in the presence of an RNase inhibitor to prepare a suspension thereof; characterized by involving no procedure of separating cell components from the biological sample.

Here, said collected biological sample is preferably frozen.

Moreover the present invention is the method described above, wherein the RNase inhibitor is guanidine thiocyanate.

Also, the present invention is the method described above, wherein the biological sample is feces.

Further, the present invention is a tumor marker detecting method for diagnosing colon cancer, comprising the following processes in addition to the process described above:

b) a process to extract RNA from the obtained sample for extracting RNA;
c) a process to reverse transcribe the extracted RNA to give cDNA;
d) a process to amplify the obtained cDNA; and,
e) a process to detect the amplified cDNA.

The present invention is a tumor marker detecting method for diagnosing colon cancer, wherein said tumor marker is COX-2.

The present invention is also a kit for preparing a sample to extract RNA used in the tumor marker detecting method for diagnosing colon cancer, comprising the following means;

a) a means to homogenize the collected biological sample in the presence of an RNase inhibitor, to prepare a suspension thereof;

said kit being characterized by involving no means of separating cell components from the biological sample.

Also, the kit of the present invention preferably contains a means to freeze said collected biological sample.

The present invention is the kit described above, wherein the RNase inhibitor is guanidine thiocyanate.

The present invention is also the kit described above, wherein the biological sample is feces.

Moreover, the present invention is a tumor marker detecting kit for diagnosing colon cancer, comprising the following means:

b) a means to extract RNA from the obtained sample for extracting RNA;
c) a means to reverse transcribe the extracted RNA to give cDNA;
d) a means to amplify the obtained cDNA; and,
e) a means to detect the amplified cDNA.

Further, the present invention is the kit described above, wherein said tumor marker is COX-2.

THE BEST MODE FOR CARRYING OUT THE INVENTION

Figure 1:
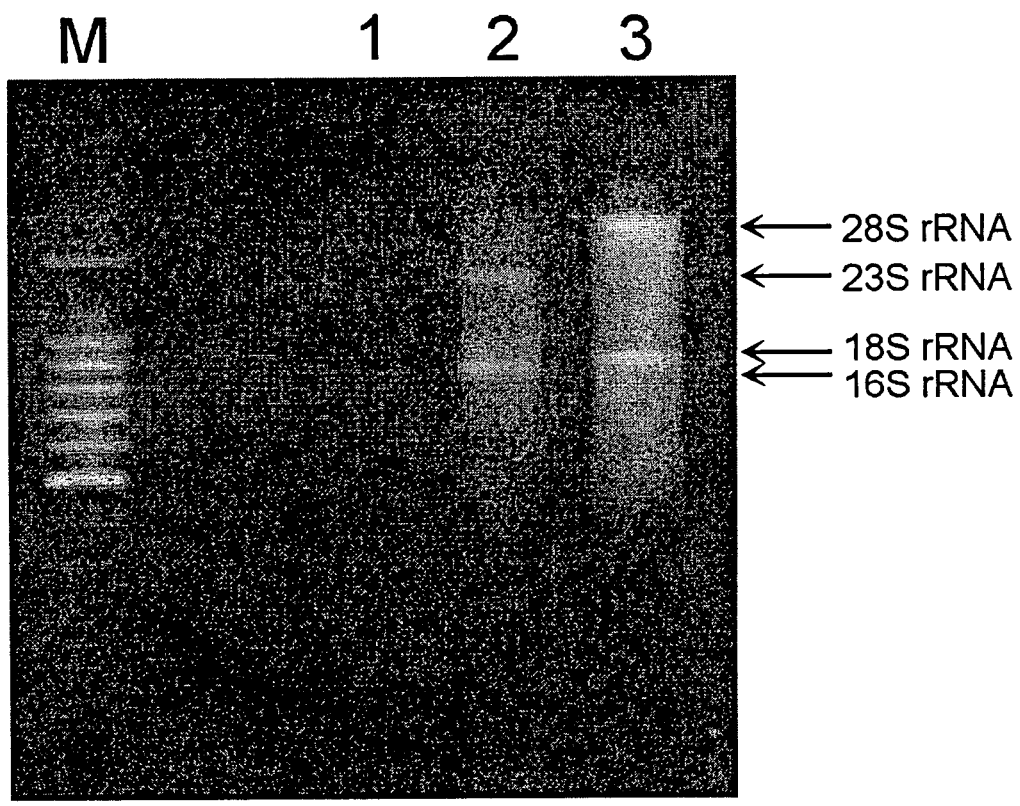
FIG. 1 shows a result of an electrophoresis in Example 2. The lane 1 shows total RNA extracted from human feces with the method by Alexander et al. The lane 2 shows total RNA extracted from human feces with the method of the present invention. The lane 3 shows total RNA extracted from a human colon cancer tissue. The lane M shows the molecular weight markers.

As for the RNase inhibitors of the present invention, guanidine thiocyanate, Isogene (a homogenous liquid containing phenol and guanidine thiocyanate), Ultraspec II (a registered trade mark) (a 14M solution of guanidine salts, urea and a RNA binding resin) and the like are included.

The biological samples of the present invention are tissues of animals and plants, body fluids, excrements and the like, and preferably are feces, and more preferably are human feces.

The biological samples of the present invention can be used as they are, or, in some cases, after frozen.

Freezing methods can be any conventional methods, and preferably a method using liquid nitrogen. The freezing (and preserving) temperature is $-1$ to $-196°$ C., preferably $-20$ to $-196°$ C., preferably $-75$ to $-196°$ C., more preferably $-110$ to $-196°$ C., and most preferably $-196°$ C.

The frozen sample may be preserved in frozen state. The preservation temperature is $-75$ to $-196°$ C., preferably $-110$ to $-196°$ C., and more preferably $-196°$ C. The preservation period is one day to 10 years, preferably one day to 3 years, and more preferably one day to one year.

The tumor marker used in the present invention is COX-2, matrixmetalloprotease (MMP), c-met, CD44 variants, EGF-R, EF-1, Wnt-2, Bradeion, SKP2, KPC-1, KPC-2, PRL-3, Angiogenin, Integrin, Snail, Dysadherin, or the like, and is preferably COX-2.

The processes c) to e) described above are called as the RT-PCR method, and can be carried out, for example, according to the description by T. Sekiya et al. eds., Forefront of PCR method, 1997, Kyoritu Pub., 187-196.

Extraction of RNA from the suspension can be carried out using methods well known in the art, and using commercially available kits, for example, RNeasy Mini (QIAGEN) or RNA Extraction Kit (Pharmacia Biotech).

"Reverse transcription" in the present invention means conversion of RNA to the complementary DNA (cDNA) using a reverse transcriptase. The reverse transcription reaction is usually conducted using a solution containing a buffer, salts such as $MgCl_2$, KCl, and the like, dithiothreitol (DTT), a primer, kinds of deoxyribonucleotides, RNase inhibitors, and a reverse transcriptase. The salts described above can be appropriately replaced by other salts after testing. Proteins such as gelatine, albumin or the like, or detergents can also be added.

For amplification of cDNA carried out subsequent to the reverse transcription, the PCR technique is usually adopted. The PCR reaction mixture usually contains a buffer, salts such as $MgCl_2$ and KCl, primers, kinds of deoxyribonucleotides, and a heat resistant polymerase. The salts described above can be appropriately replaced by other salts after testing. Proteins such as gelatine, albumin or the like, dimethylsulphoxide, detergents, or the like, can also be added.

For amplification of cDNA, the LAMP method (Japan Patent No. 3313358) or the ICAN method (Japan Patent Laid-Open No. 2001-136965) can be used.

A "primer" in the present invention means an oligonucleotide which works as a synthesis initiation point in the case of cDNA synthesis or polynucleotide amplification. The primer is preferably a single-strand, but a double-strand can also be used. When the primer is a double-strand, it is preferable to make it single-stranded prior to the amplification reaction. The primer can be synthesized according to a method well known in the art, or can be isolated from the living organisms.

The reverse transcriptase used in the reverse transcription reaction is an enzyme capable of reverse transcribing RNA to cDNA. As for the reverse transcriptase, there are reverse transcriptases derived from retroviruses such as RAV (Rous associated virus), AMV (Avian myeloblastosis virus) and the like, and reverse transcriptases derived from mouse retroviruses such as MMLV (Moloney murine leukemia virus) and the like, but it is not limited to the aboves.

As the heat resistant polymerase used for PCR, Taq polymerase can be nominated, but it is not confined to this.

As the detection method of amplified DNA, electrophoresis using agarose gel can be used, but the method may not be confined to this.

Further, the kit according to the present invention may contain an instruction describing the methods of the present invention.

EXAMPLE 1

The following examples illustrate the present invention, but do not limit the invention.

Among patients hospitalized in the First Department of Internal Medicine of Hamamatsu University School of Medicine for detailed examination and therapy, 30 cases confirmed to have colon cancer and 22 cases to have no tumor or inflammatory alteration in their colon (non colon disorder) by the total colonoscopy were selected as the subject of the study. Informed consents of all the cases had been obtained.

As soon as possible after sampling feces, the feces were separated into 5 ml tubes about 1 g each, were frozen using liquid nitrogen, and were stored at $-80°$ C. Also, for comparison and reference, human hemoglobin (Hb) in the feces of each sample was measured by the immunological fecal occult blood test. Tissue biopsy specimen, taken both from the cancer and the normal parts when the endoscopy was carried out before the therapy, were frozen by liquid nitrogen and stored at −80° C. Then, feces were homogenized using a homogenizer, guanidine salt, and phenol, and whole RNA was extracted using chloroform and ethanol.

One µg of the obtained RNA was reverse transcribed using ReverScript II (a registered trade mark), (reaction mixture volume: 20 µl, Wako Pure Chemical Industries) to give cDNA. A part thereof was amplified by means of nested PCR using GeneTaq (Wako). The PCR product obtained was electrophresed on 4% agarose gel, and stained by ethidium bromide.

Here, the primers used were: the random primers in reverse transcription, and in PCR, were those reported by Gerhard (JJCO, 1994) for CEA, and were originally designed for COX-2. The first round of PCR was executed 20 cycles, and the second round 25 cycles.

The followings indicate the primers used.

<CEA>

TABLE 1

| Forward 1: | 5'-TCTGGAACTTCTCCTGGTCTCTCAGCTGG-3' (SEQ ID NO: 1) |
|---|---|
| Forward 2: | 5'-GGGCCACTGCTGGCATCATGATTG-3' (SEQ ID NO: 2) |
| Reverse: | 5'-TGTAGCTGTTGCAAATGCTTTAAGGAAGAAGC-3' (SEQ ID NO: 3) |

<COX-2>

TABLE 2

| Forward 1: | 5'-CTGAAAACTCCAAACACAG-3' (SEQ ID NO: 4) |
|---|---|
| Forward 2: | 5'-GCACTACATACTTACCCACTTCAA-3' (SEQ ID NO: 5) |
| Reverse: | 5'-ATAGGAGAGGTTAGAGAAGGCT-3' (SEQ ID NO: 6) |

Results

Feces from 30 colon cancer cases (3 early cancer and 27 advanced cancer cases) and from 22 cases in the control group were examined by RT-PCR, in order to detect CEA and COX-2, and the following results were obtained.

CEA was detected in all cases among the 30 colon cancer cases, and in 21 among 22 cases in the control group. Also, it turned out that RNA suitable for RT-PCR amplification could be extracted from both samples.

COX-2 was detected in 27 cases among the 30 colon cancer cases (caeca: 2/2, ascending colon: 3/5, descending colon: 1/1, sigmoid colon: 7/7, rectum: 12/13; early cancer: 2/3, advanced cancer: 25/27), but was not detected in any of 22 cases in the control group (sensitivity: 90%, specificity: 100%).

In the immunological fecal occult blood test, 23 among 28 colon cancer cases and 3 among 22 control cases were positive (sensitivity: 82.1%, specificity: 86.3%).

Among three COX-2 negative colon cancer cases, one was positive in the immunological fecal occult blood test, and 2 were negative.

COX-2 was detected in 3 among 5 colon cancer cases negative to the immunological fecal occult blood test,

EXAMPLE 2

The amount and the distribution of molecular weights of total RNA obtained from human feces according to the method of the present invention were compared with those obtained according to Alexander's method (R. J. Alexander and R. F. Raicht, Digestive Diseases and Sciences, 43(12), 1998, 2652-2658). As a control, total RNA was extracted from the human colon cancer tissues using a commercially available RNA extraction reagent (ISOGEN, Wako)

The same amount of total RNA extracted from each sample was electrophoresed on an agarose gel.

Two main bands recognized on the lane 3 (RNA derived from human colon cancer tissues) show 28s and 18s rRNAs. Smeared parts thereon indicate that various kinds of high molecular weight RNAs are contained in the obtained total RNA.

Two main bands recognized on the lane 2 (RNA derived from feces obtained by the method of the present invention) show 23s and 16s rRNAs derived from enteric bacteria. Since smeared parts were also recognized thereon similarly to the lane 3, the total RNA obtained from the feces by the method of the present invention is considered to contain also various kinds of high molecular weight RNAs.

Contrarily, any bands and smears were not detected at all in the lane 1, showing that high molecular weight RNAs were not contained in the extract of the sample.

In fact, the desired products were obtained from the sample of lane 2 by the RT-PCR technique, but no PCR products were obtained from the sample of lane 1.

From the results of the present studies, it became obvious that the RNA extracted from the human feces by the method of the present invention can be amplified by means of the RT-PCR technique. Also, the detection of COX-2 from the feces by the RT-PCR technique had 90% sensitivity and 100% specificity, and it is proved that the present invention is superior to a conventional technique of the immunological fecal occult blood test.

Further, since the method of the present invention needs smaller amount of feces for detection and has higher detection sensitivity compared to the detection of the gene mutation of APC, K-ras, or p53, it can save largely the time and effort needed for the detection.

While the conventional technique of the fecal occult blood test targets a general and indirect event, "bleeding" from the lesion, the method of the present invention targets a specific and direct event, the expression of a marker of carcinogenesis, COX-2. Therefore, the data obtained by the method of the present invention provide diagnosis with higher quality.

Accordingly, the method of the present invention is clinically very useful as a novel non-invasive screening method with high specificity and high sensitivity.

The invention claimed is:

1. A method, comprising:
a) homogenizing collected feces of a person in the presence of an RNase inhibitor to prepare a suspension thereof, without separating cell components from the feces;
b) extracting RNA from the suspension from step a) to provide extracted RNA;
c) carrying out reverse transcription on the extracted RNA from step b) to provide cDNA;
d) amplifying the cDNA from step c);
e) detecting the expression level of COX-2 in the amplified cDNA from step d), and
f) determining that the person has colon cancer if COX-2 is expressed in the amplified cDNA.

2. The method according to claim 1, wherein the feces is frozen.

3. The method according to claim 1, wherein the feces is human feces.

4. The method of claim 1, wherein the RNase inhibitor is a guanidine salt.

5. The method of claim 1, wherein the RNA extracted in step (b) is total RNA including prokaryotic RNA and eukaryotic RNA.

* * * * *

SEQUENCE LISTING

<160> NUMBER OF SEQ ID NOS: 6

<210> SEQ ID NO 1
<211> LENGTH: 29
<212> TYPE: DNA
<213> ORGANISM: Artificial
<220> FEATURE:
<223> OTHER INFORMATION: designed primer

<400> SEQUENCE: 1
tctggaactt ctcctggtct ctcagctgg                              29

<210> SEQ ID NO 2
<211> LENGTH: 24
<212> TYPE: DNA
<213> ORGANISM: Artificial
<220> FEATURE:
<223> OTHER INFORMATION: designed primer

<400> SEQUENCE: 2
gggccactgc tggcatcatg attg                                   24

<210> SEQ ID NO 3
<211> LENGTH: 32
<212> TYPE: DNA
<213> ORGANISM: Artificial
<220> FEATURE:
<223> OTHER INFORMATION: designed primer

<400> SEQUENCE: 3
tgtagctgtt gcaaatgctt taaggaagaa gc                          32

<210> SEQ ID NO 4
<211> LENGTH: 19
<212> TYPE: DNA
<213> ORGANISM: Artificial
<220> FEATURE:
<223> OTHER INFORMATION: designed primer

<400> SEQUENCE: 4
ctgaaaactc caaacacag                                         19

<210> SEQ ID NO 5
<211> LENGTH: 24
<212> TYPE: DNA
<213> ORGANISM: Artificial
<220> FEATURE:
<223> OTHER INFORMATION: designed primer

<400> SEQUENCE: 5
gcactacata cttacccact tcaa                                   24

<210> SEQ ID NO 6
<211> LENGTH: 22
<212> TYPE: DNA
<213> ORGANISM: Artificial
<220> FEATURE:
<223> OTHER INFORMATION: designed primer

<400> SEQUENCE: 6
ataggagagg ttagagaagg ct                                     22